United States Patent [19]

Rogers et al.

[11] 4,043,292
[45] Aug. 23, 1977

[54] MICROSCOPE SLIDE STAINING APPARATUS HAVING TEMPERATURE CONTROL

[75] Inventors: Charles H. Rogers; Kevin J. Sullivan, both of Raleigh, N.C.

[73] Assignee: Corning Glass Works, Corning, N.Y.

[21] Appl. No.: 597,442

[22] Filed: July 21, 1975

[51] Int. Cl.² .................. B05C 5/00; B05C 15/00
[52] U.S. Cl. .............................. 118/5; 118/59; 118/64; 118/319; 118/642
[58] Field of Search ............... 118/5, 642, 58, 59, 118/64, 66, 401, 319; 427/2; 134/80, 81, 57 R, 105

[56] References Cited

U.S. PATENT DOCUMENTS

| | | | |
|---|---|---|---|
| 3,186,694 | 6/1965 | Beggs | 118/5 X |
| 3,267,902 | 8/1966 | Pritchard et al. | 118/642 |
| 3,349,222 | 10/1967 | Johnston | 118/59 |
| 3,391,670 | 7/1968 | Lester et al. | 118/5 |
| 3,807,353 | 4/1974 | Kobernick | 118/5 |
| 3,853,092 | 12/1974 | Amos et al. | 118/56 |

*Primary Examiner*—John P. McIntosh
*Attorney, Agent, or Firm*—William J. Simmons, Jr.; Walter S. Zebrowski; Clarence R. Patty, Jr.

[57] ABSTRACT

Method and apparatus for staining biological specimens by forming a film of staining reagents on the surface of the specimen containing slide. Heating means raises the temperature of the staining reagents on the slide. The temperature of the reagent film is determined, and a feedback signal to the heating means accurately maintains the temperature of the film within a predetermined range.

13 Claims, 8 Drawing Figures

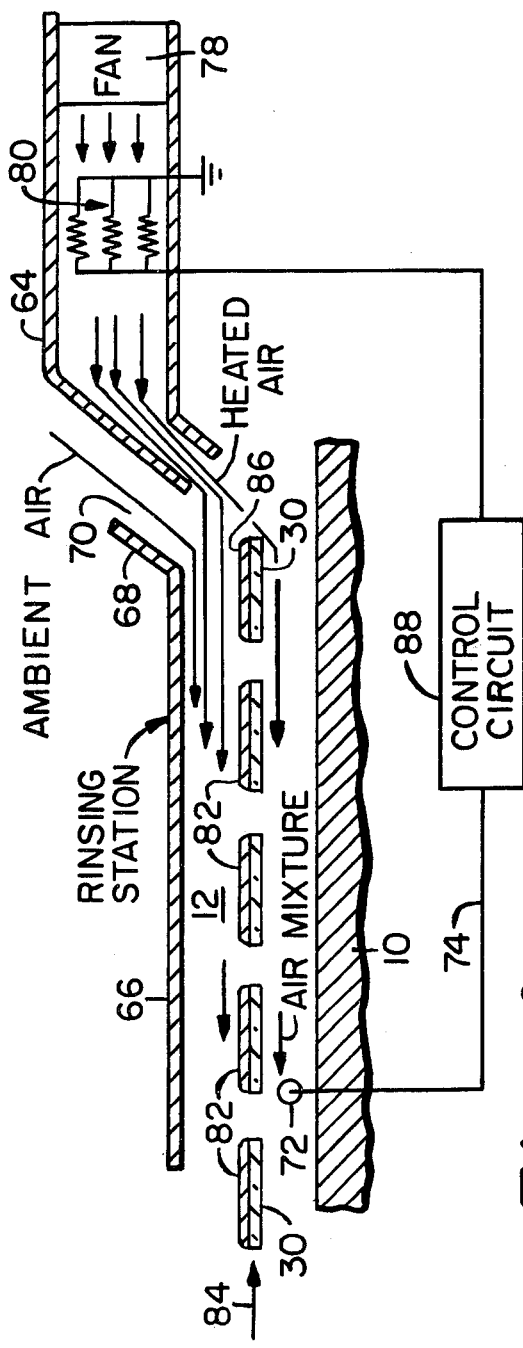
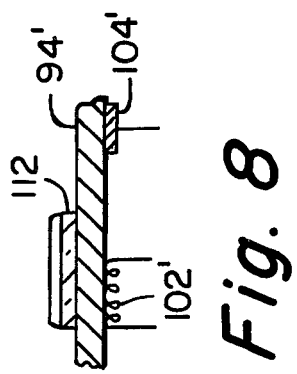
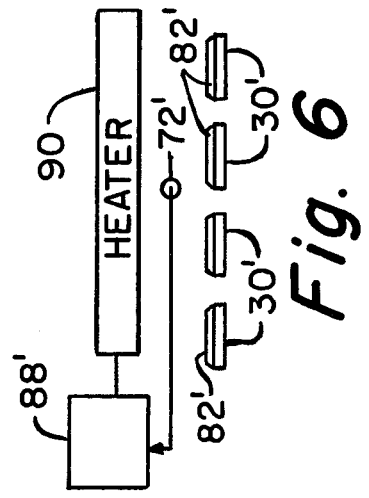
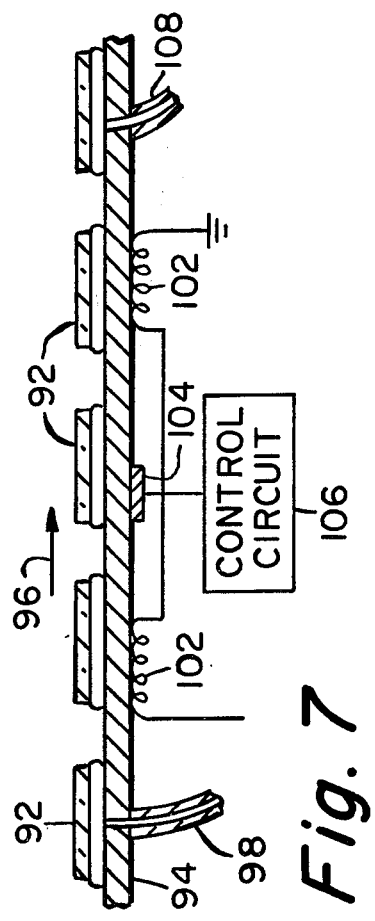

MICROSCOPE SLIDE STAINING APPARATUS HAVING TEMPERATURE CONTROL

BACKGROUND OF THE INVENTION

This invention relates to an apparatus for staining microscope slides and more particularly to an apparatus for maintaining the temperature of a reagent film on a microscope slide at an elevated temperature within a predetermined range.

In the microscopic examination of certain material, particularly cellular materials such as blood, tissue, or the like, a specimen of the material is placed on a transparent microscope slide. Thereafter, the material is stained by contacting it with solutions which stain or dye only certain constituents of the cell to provide a contrast which facilitates visual examination. Microscope slides are presently being stained by both manual and automated techniques. To manually stain a slide it is submersed successively in bulk reagents, each reagent remaining in contact with the specimen for a predetermined time before the specimen is submersed into a succeeding reagent solution. The slide is then rinsed and dried.

Because of the excessive amount of time required for hand staining and due to the fact that contamination can be caused by submersing many slides in the same container of solution, mechanized means are being increasingly employed for staining microscope slides. This type of apparatus conveys the slides through a plurality of stations where the staining reagents are automatically applied to the specimen. For example, U.S. Pat. No. 3,431,886 issued to J. B. McCormick et al. teaches an apparatus for conveying slides in a horizontal position over a flat liquid-applying surface and injecting a treating liquid into the space between the slide and surface. The slides are then moved into a vertical position for draining and drying. Another automatic staining apparatus is disclosed in U.S. Pat. No. 3,853,092 issued to L. G. Amos et al. This apparatus conveys the microscope slides in a circular path and automatically dispenses a metered amount of various reagents on the upper surface of the slides. The apparatus also imparts a nutating motion to the slide to effect uniform wetting of the top surface thereof by each reagent and by the rinse. The slides are thereafter moved to a near vertical position for draining and drying.

By controlling the time during which the specimen is subjected to each reagent and by carefully metering the amount of reagents applied, the stained specimens exhibit sufficient contrast for visual analysis. For example, laboratory technicians can perform what is referred to as a white blood cell differential by counting the leukocytes on a stained blood smear. Because of the amount of time required for a technician to analyze a biological specimen and due to the increasing number of analyses being performed, automation of tests such as the white blood cell differential is inevitable. A thesis by J. W. Bacus, "An Automated Classification of the Peripheral Leukocytes by Means of Digital Image Processing", University of Illinois, Chicago, 1971, describes one automated system. A system for automatically scanning and digitizing the count of leukocytes on a stained smear is disclosed in copending application Ser. No. 353,004 entitled "Image Scanning Converter for Automated Slide Analyzer" filed by D. A. Cotter on Apr. 20, 1973 now U.S. Pat. No. 3,883,852 issued May 13, 1975.

The accuracy with which automated slide analysis can be performed depends upon the reproducibility of the slide staining process. Each blood film, for example, should be stained so that the optical density of a given type of nucleus substantially achieves a specified value. Furthermore, the staining process should provide optimal contrast between the cell nucleus and cytoplasm.

SUMMARY OF THE INVENTION

In accordance with this invention an apparatus for staining biological specimens comprises means for supporting a microscope slide having a biological specimen disposed on one surface thereof. Means are provided for forming a film of staining reagents on the surface of the slide. Means are provided for controlling the temperature of the reagent film during the staining process. By maintaining the reagent film at an elevated temperature, stain uptake by the cell nuclei has been enhanced, thereby increasing the contrast between the cell nucleus and cytoplasm. Furthermore, greater reproducibility in the optical density of the stained nuclei has been achieved by closely controlling this elevated temperature.

BRIEF DESCRIPTION OF THE DRAWINGS

FIG. 4 is a schematic illustration of an air temperature control system of the type employed in conjunction with the embodiment of FIG. 1.

FIG. 6 is a schematic representation in block diagram form of another embodiment of the present invention.

FIGS. 7 and 8 are schematic representations of other embodiments of the present invention.

DETAILED DESCRIPTION

Figure 1:
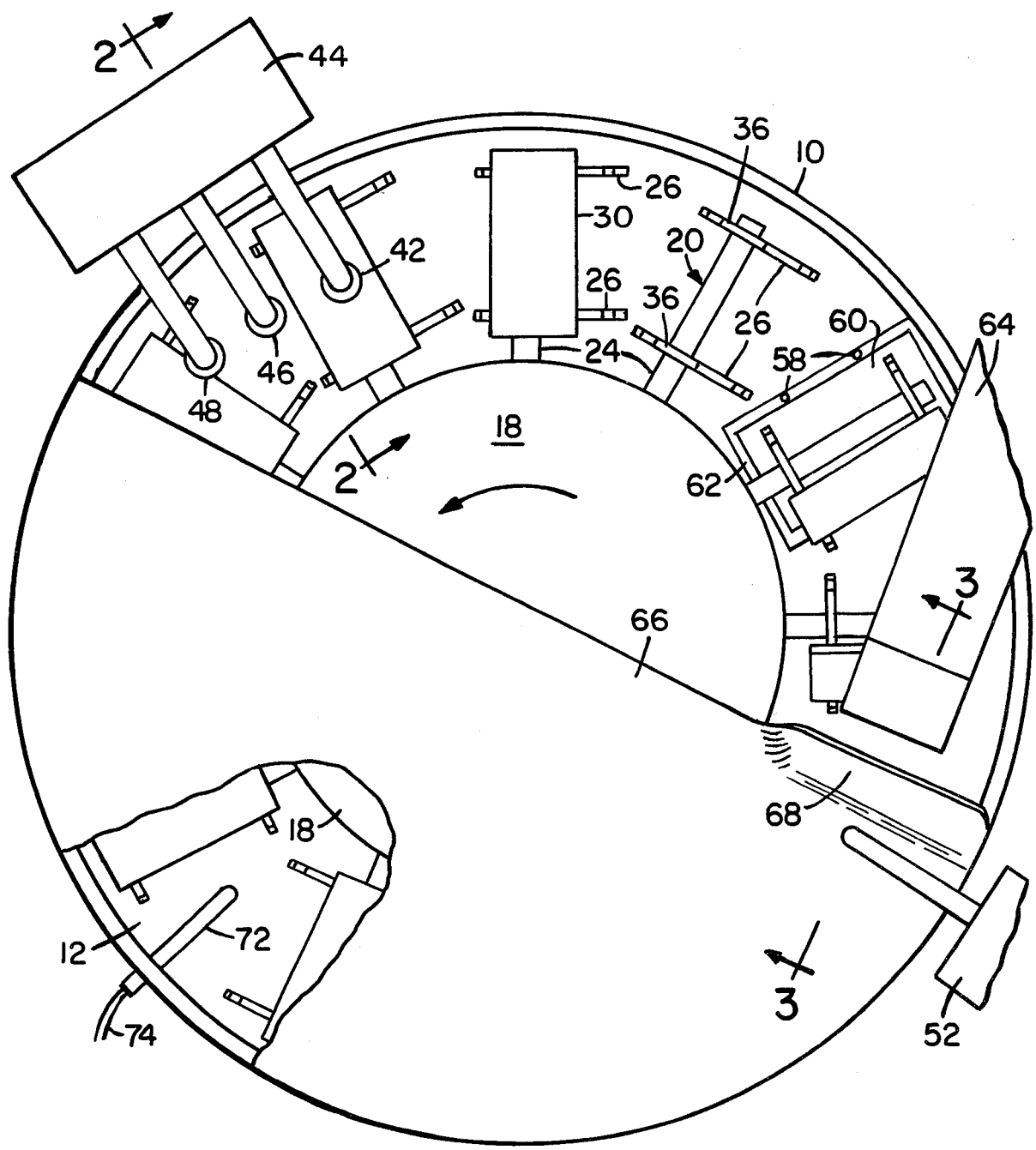
FIG. 1 is a plan view of one embodiment of the present invention.
Figure 2:
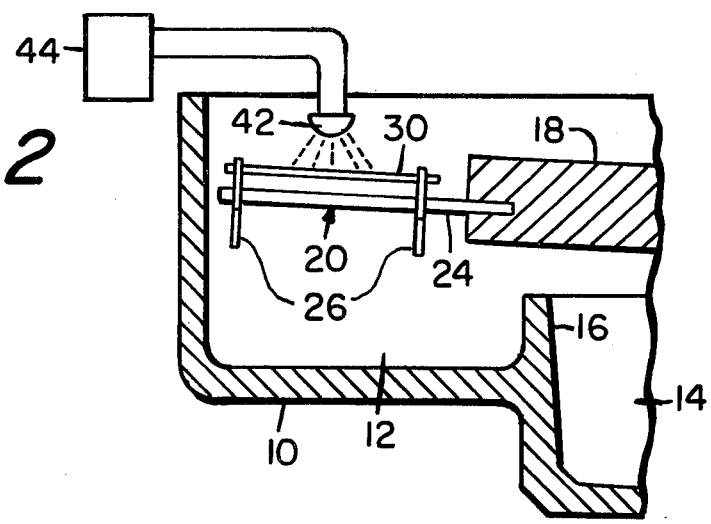
FIG. 2 is a fragmentary elevation, partly in section, of the apparatus of the present invention taken along lines 2—2 of FIG. 1.

The preferred embodiment of the present invention is particularly adaptable to a slide staining apparatus of the type disclosed in the aforementioned Amos et al. patent which is incorporated herein by reference. Referring to FIGS. 1 and 2, there is shown a housing 10 which is divided by cylindrical wall 16 into peripheral compartment 12, within which blood slides are treated, and central compartment 14, which houses at least a portion of the apparatus driving mechanism. Supported above compartment 14 is a nutating ring 18 to which a plurality of flight assemblies 20 are attached. Each flight assembly comprises arm 24 and at least a pair of support members 26. As is specifically described in said Amos et al. patent application nutating ring 18 is tilted an appreciable number of times during each complete rotation thereof. Thus, microscope slides 30, which are disposed on supports 26, are conveyed along a circular path in peripheral compartment 12.

Slides 30 are placed on support members 26 with the biological specimens on the upper surfaces thereof. As nutating ring 18 is caused to nutate, slides 30 are caused to rotate and come under the first nozzle 42 of reagent or reactant dispenser 44. As shown in FIG. 1, reactant dispenser 44 is illustrated as a three compartment dispenser with each compartment containing one of three reagents which are dispensed by means of three nozzles 42, 46 and 48. For the treatment of a microscope blood slide, such reactants may be a fixative, dye and buffer. Such blood reagents or reactants and their purposes are well known in the art. The cross-sectional view of FIG. 2 shows one of the reagents being dispensed from nozzle 42 to the upper specimen containing surface of microscope slide 30. Whereas means are illustrated for dispensing three reagents onto the slides, it is known that as few as one staining solution may be applied to a slide to stain a specimen disposed thereon. Moreover, the staining solution need not be applied after the slides are placed on supports 26. For example, the slides may be dipped into a vat of staining solution and thereafter placed on supports 26 with the solution covered specimens on the upper surfaces thereof.

Figure 3:
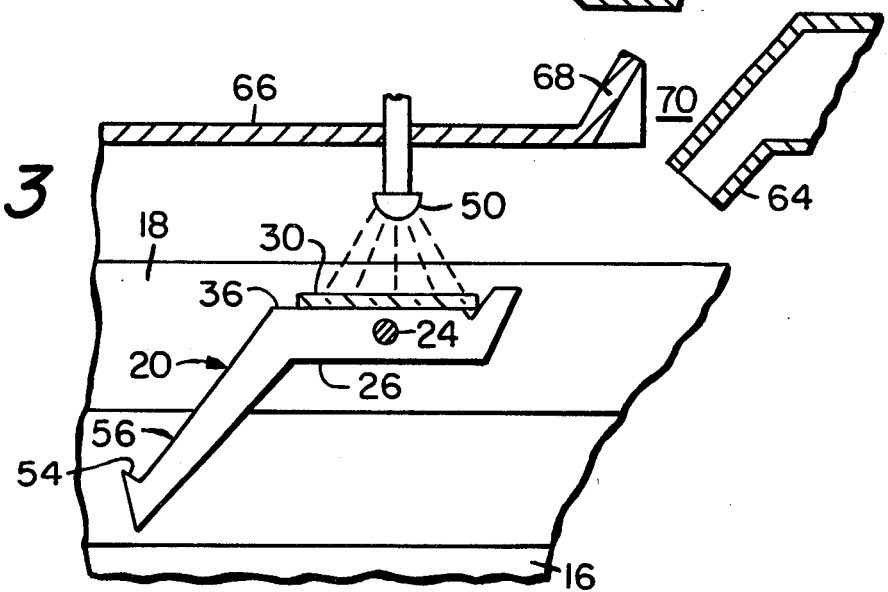
FIG. 3 is a fragmentary elevation, partly in section, of the apparatus of the present invention taken along lines 3—3 of FIG. 1.

After all of the desired reagents are applied to the top surface of microscope slide 30, these reagents are permitted to act upon the specimen for a substantial portion of the rotation of the nutating ring. That is, the reagents act upon the slide specimen from the time they are applied to the surface of the microscope slide until they are rinsed or otherwise removed therefrom. As is seen from FIGS. 1 and 3, the reagents may be rinsed from the microscope slide by means of rinse nozzle 50 which is connected to a suitable supply of rinsing solution, e.g., water, dispensed from rinsing solution dispenser 52. Reagents could also be removed from a slide by spinning it.

After slide 30 is rinsed, it continues to rotate through peripheral compartment 12. The slide may then be manually removed or it may be automatically removed by means such as that disclosed in said Amos et al. patent. In accordance with that patent means (not shown) engage slide 30 after it passes the rinsing station, thereby causing microscope slide 30 to slide along upper surface 36 of support member 26 until it reaches step 54 which projects from the bottom of surface 56 (see FIG. 3). As the slide continues to rotate through compartment 12 while being supported by surface 56, the rinsing solution and any remaining reagents are permitted to be drained off. The slide may then be automatically removed by engaging removal arms 58 which are mounted adjacent opening 60 in housing 10, which opening is defined by wall 62.

During the time that the microscope slides are rotated from the reagent dispensing station to the rinsing station, evaporation of the reagents causes cooling, and differences in ambient conditions can therefore influence the temperature of the reagent film. It has been found that reagent film temperature is one of the parameters that must be controlled to obtain reproducible stain uptake. The apparatus of FIG. 1 subjects the reagent film to a predetermined reproducible temperature profile until the slide is rinsed. The reagent films disposed upon the upper surfaces of the slides progressing between the last reagent dispensing nozzle 48 and rinse nozzle 50 are heated by warm air flowing from duct 64. A cover 66 of plastic, sheet metal or the like cooperates with the walls forming peripheral compartment 12 to form a duct which confines the warm air supplied by duct 64. Since duct 64 is disposed along the peripheral compartment 12 after the rinsing station, air flowing therefrom initiates the process of drying the surface of slides 30. Warm air duct 64 is so disposed that ambient air is entrained with the warm air flowing therefrom, and it is this mixture of warm and ambient air which heats the reagent films to the desired temperature. Cover 66 may be provided with an air scoop 68 adjacent to duct 64 to provide a channel 70 through which entrained ambient air flows.

Since ambient conditions greatly influence the equilibrium temperature of the reagent film, a temperature sensor 72 is disposed in peripheral compartment 12 to sense the temperature of the air mixture flowing past those of slides 30 containing a reagent film. Sensor 72 may be located in the upper part of the housing side wall so that it extends into compartment 12 just above the path of the moving slides 30. The particular location of the sensor is not critical, but it is preferred that it be located as close as possible to slides 30. Improved temperature control regardless of changes in environmental temperature and relative humidity can be obtained by employing the sensor disclosed in copending U.S. patent application Ser. No. 597,323 entitled "Apparatus for Controlling of the Temperature of a Liquid Body" filed by C. H. Rogers et al. on even date herewith. Sensor 72 is connected by a cable 74 to a control system which regulates the temperature of the warm air flowing from duct 64.

FIG. 4 is a schematic illustration of an air temperature control system of the type employed in conjunction with the embodiment of FIG. 1. A fan 78 blows ambient air over resistance heater 80, thereby causing heated air to flow from duct 64. Ambient air flows through channel 70 and becomes entrained with heated air. The resultant air mixture flows in the direction of the arrows through the duct formed by cover 66 and housing 10. Microscope slides 30 having a reagent film 82 thereon move in the direction of arrow 84. Reagent film 82 is rinsed from each slide 30 at the rinsing station, thereby forming a water film 86 on the slide surface. The heated air flows toward water film 86 and initiates the drying process. The heated air and entrained ambient air form the air mixture which flows over and heats reagent films 82. The temperature of the air mixture is sensed by sensor 72 which provides a control signal to control circuit 88 by way of cable 74. This control signal causes an adjustment of the power supplied by the control circuit to resistace heater 80.

Depending upon the particular type of biological specimen which is to be stained and the type of staining reagents employed, the maximum and minimum temperatures of the reagent film may be specified. The temperature profile along peripheral compartment 12 between the reagent dispensing and rinsing stations is determined by such parameters as power flowing to resistance heater 80, air flow provided by fan 78, and temperature and flow rate of ambient air.

The following example relates to the operation of the apparatus of the present invention for staining blood samples. Nutating ring 18 rotates at 1/12th of a revolution per minute. The process details are set forth in Table 1.

TABLE I

| Step | Reagent | Quantity | pH | Step Duration | Temperature |
|------|---------|----------|-----|---------------|-------------|
| 1 | fix | 0.4 ml | 7.0 | 1 minute | less than 35° C |
| 2 | stain | 0.35 ml | 7.0 | 1 minute | less than 35° C |
| 3 | buffer | 1.0 ml | 6.8 | 6 minutes | 28° C peak (26° C ± 1° avg.) |
| 4 | rinse | 200.0 ml | 6.8–7.2 | 18 seconds | not controlled |
| 5 | dry | — | — | 2 minutes | 45–55° C |

The fix, stain and buffer reagents are applied to the upper surface of each slide by nozzles 42, 46 and 48, respectively. The one minute duration given for steps 1 and 2 indicates that that particular reagent is permitted to act upon the biological specimen for the stated time before the next reagent is added. For example, after the fix is sprayed on the surface of the slide, it is permitted to remain there for one minute during which time the slide rotates from nozzle 42 to nozzle 46. At this point in the rotation of the slide, the stain is sprayed onto the slide and mixes with the fix. One minute later, the slide has been rotated to a position under nozzle 48 where the buffer is sprayed thereon. The temperature listed for step 3 was found to enhance the contrast between the cell nucleus and cytoplasm and to enable greater reproducibility in the staining process.

Figure 5:
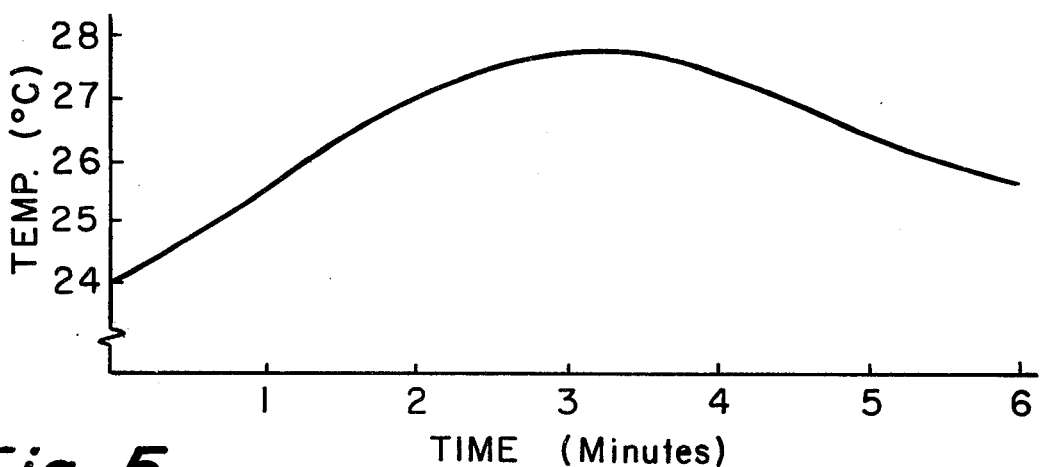
FIG. 5 is a graph of a typical temperature profile of a reagent film as it progresses through an automatic slide staining apparatus.

FIG. 5 shows a temperature profile of a reagent film during processing. In this particular example, the average temperature was 26.2° C. The temperature of the reagent film was about 24° C immediately following application of the buffer to the slide. Between three and four minutes after the buffer was applied, a maximum temperature of slightly more than 27° C was achieved. Ambient temperature was 24° C, and the relative humidity was 70%.

Without the temperature control system of the present invention stain uptake in the leukocyte nucleus varied in accordance with ambient conditions. To illustrate the improvement in the staining process as a result of controlling the temperature of the reagent film, slides were stained by a process in which reagent film temperature was controlled and the results were compared with slides stained by a process similar to the first process except that reagent film temperature control was not employed. About 50 cells were examined on five slides stained by the controlled temperature process. The mean optical density of the monocyte nucleus was 0.88 and the standard deviation was 0.02. A similar number of cells stained without temperature control exhibited an optical density of about 0.83 with a standard deviation of 0.055. It is seen that the temperature control system of the present invention results in greater monocyte nucleus optical density and greater uniformity of staining.

Another embodiment of an apparatus for heating a reagent film disposed on the specimen-containing surface of a microscope slide is illustrated in FIG. 6 wherein elements similar to those of FIGS. 1–4 are represented by primed reference numerals. In this embodiment reagent films 82' disposed upon the surfaces of slides 30' are heated by radiant energy provided by heater 90. Sensor 72' senses the temperature in the vicinity of reagent films 82' and provides a signal to control circuit 88' which controls the amount of heat energy radiated from heater 90. Slides 30' may be transported past heater 90 by an apparatus such as that described in conjunction with FIGS. 1–4, or they could be manually placed under heater 90 and allowed to remain there for a predetermined time.

In the embodiment illustrated in FIG. 7 microscope slides 92 are slowly advanced across platen 94 in the direction of arrow 96. The various reactants are applied to the specimen-containing surfaces of the slides through orifices in the platen. The reagent dispensing means and slide advancing means may be of the type disclosed in the aforementioned U.S. Pat. No. 3,431,886. As a slide having a film of other reagents disposed between platen 94 and the surface thereof becomes disposed adjacent to the orifice to which tube 98 is connected, a measured amount of buffer is applied to the slide surface. As the slides are advanced across the surface of platen 94, which may consist of stainless steel, synthetic resin polymers or the like, the reagent film, which adheres to the slide surface by surface tension, moves along with the slide.

In accordance with the present invention, platen 94 is heated by means of heating elements such as resistance windings 102 to maintain the temperature of the reagent films within a predetermined range. Sensor 104 provides a signal to control circuit 106 which controls the power flowing through heating elements 102. When a slide becomes positioned adjacent to the orifice associated with tube 108, the reagent film is rinsed therefrom by a rinsing solution flowing from that tube.

In the embodiment illustrated in FIG. 8 elements similar to those of FIG. 7 are represented by primed reference numerals. Slides 112 are disposed on heated platen 94' with the specimen and reagent film on that side of the slide opposite the platen. Heat from the platen is conducted through the slide to the reagent film.

Although the present invention has been described with respect to specific details of certain embodiments thereof, it is not intended that such details be limitations upon the scope of the invention except insofar as set forth in the following claims.

We claim:
1. An apparatus for staining biological specimen-containing microscope slides comprising
   microscope slide support means having means for conveying a plurality of slides along a predetermined path,
   means disposed along said predetermined path for introducing a metered amount of at least one staining reagent on only that surface of said slide on which said specimen is disposed to form a reagent film,
   means disposed along said path for maintaining the temperature of said reagent film within a given range of temperature for a given period of time, and
   means disposed along said path for removing said reagent film from said slides at the expiration of said given period of time.
2. The apparatus of claim 1 further comprising sensor means for providing an indication of the temperature of said reagent film, and a control circuit responsive to the output of said sensor means, the output of said circuit being connected to said temperature maintaining means.
3. The apparatus of claim 2, wherein said temperature maintaining means comprises means for blowing heated air onto said slides.
4. The apparatus of claim 2 wherein said temperature maintaining means comprises means for radiating heat energy onto said reagent film.
5. The apparatus of claim 2 wherein said temperature maintaining means comprises means for disposing a heated surface in contact with said reagent film.
6. The apparatus of claim 2 wherein said temperature maintaining means comprises means for disposing a heated surface in contact with said slide.
7. The apparatus of claim 2 wherein said means for removing comprises means for rinsing said reagent film from said slide.
8. The apparatus of claim 7 wherein said temperature maintaining means comprises means for blowing heated air onto said slides while said reagent film remains on said slides.

9. The apparatus of claim 8 wherein said means for blowing heated air is disposed along said path after said rinsing means so that the heated air therefrom flows across said rinsed slides, said heated air also flowing across those slides containing a reagent film, thereby increasing the temperature thereof.

10. The apparatus of claim 9 further comprising means for facilitating the entrainment of ambient air along with said heated air.

11. The apparatus of claim 10 further comprising a duct surrounding that portion of said path between said means for introducing and said means for rinsing.

12. An apparatus for staining biological specimen-containing microscope slides comprising means for supporting said slides so that the surface thereof on which said specimen is disposed faces upwardly, means for introducing at least one staining reagent onto at least the upper surface of said slides to form a film thereon, means for conveying said slides along a predetermined path, means for blowing heated air onto said slides to maintain the temperature of said reagent film within a given range of temperatures for a given period of time, and means disposed along said path for removing said reagent film from said slides at the expiration of said given period of time.

13. The apparatus of claim 12 wherein said means for removing comprises means for rinsing said reagent film from said slide, said means for blowing heated air being disposed along said path after said rinsing means so that the heated air therefrom flows across said rinsed slides, said heated air also flowing across those slides containing a reagent film, thereby increasing the temperature thereof.

* * * * *